United States Patent
Choi et al.

(10) Patent No.: US 6,660,908 B2
(45) Date of Patent: Dec. 9, 2003

(54) GENETIC SEQUENCES ENCODING SUBSTRATE-SPECIFIC DIHYDROFLAVONOL 4-REDUCTASE AND USES THEREFOR

(75) Inventors: Giltsu Choi, Kwangju (KR); Eric I Johnson, Pullman, WA (US); Hankuil Yi, Kwangju (KR); Byongchul Shin, Kwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 48 days.

(21) Appl. No.: 10/060,506

(22) Filed: Jan. 30, 2002

(65) Prior Publication Data

US 2002/0120959 A1 Aug. 29, 2002

Related U.S. Application Data

(62) Division of application No. 09/638,715, filed on Aug. 14, 2000, now Pat. No. 6,465,630.

(51) Int. Cl.[7] .............................. C12N 15/82
(52) U.S. Cl. .................. 800/282; 800/278; 800/287; 800/295; 800/298
(58) Field of Search ................. 800/282, 278, 800/298, 287, 295; 536/23.1

(56) References Cited

PUBLICATIONS

Helariutta et al. Plant Molecular Biology 28(5) 935–941, 1995.*

* cited by examiner

Primary Examiner—Jeffrey Fredman
Assistant Examiner—Juliet C. Switzer
(74) Attorney, Agent, or Firm—Mathews, Collins, Shepherd & McKay, P.A.

(57) ABSTRACT

The invention includes modified dihydroflavonol 4-reductase (DFR) nucleic acids encoding the modified DFR that has altered amino acid sequences at the substrate specificity determining region. The property of the modified DFR is characterized by its ability to reduce dihydrokaempferol (DHK) preferentially over dihydroquercetin (DHQ), and dihydromyricetin (DHM). The invention also includes plants having at least one cell expressing the modified DFR. Such plants are characterized by the increased content of pelargonidin-based pigments. The invention also includes vectors comprising at least a portion of the modified DFR nucleic acids. The invention also includes methods using such vectors for producing plants having the increased content of pelargonidin-based pigments.

5 Claims, 4 Drawing Sheets

FIG. 2

| | | |
|---|---|---|
| RESIDUES OF 117-176 SEQ ID NO: 1 | Gerbera | KAKTVKKRLVFTSSAGTVNGQEKQLHVYDESHWSDLDFIYSKKMTAWMYFVSKTLAEKAAW |
| SEQ ID NO: 13 | Lilium | KAGTVKRVIFTSSAGTVNVQENQMPEYDESSWSDVDFCRRVKMTGWMYFVSKTLAEKAAW |
| SEQ ID NO: 14 | Hordeum | EAGTVKRIVFTSSAGSVNIEERPRPAYDQDNWSDIIDYCRRVKMTGWMYFVSKALAEKAAW |
| SEQ ID NO: 15 | Antirrhinum | QAKTVKKFIFTTSGGTVNVEEHQKPVYDETDSSDMDFINSKKMTGWMYFVSKILAEKAGM |
| SEQ ID NO: 16 | Petunia | KANTVKRLVFTSSAGTLDVQEQQKLFYDQTSWSDLDFIYAKKMTGWMYFASKILAEKAAM |
| SEQ ID NO: 17 | Callistephus | KAKTVKKLVYTSSAGTVNVQETQLPVYDESHWSDLDFIYSKKMTAWMYFVSKTLAEKAAM |
| SEQ ID NO: 18 | Daucus | KAKTVKKLIYTSSAGTVNVREHQLPVYDENSWSDMDFIYSTKMTAWMYFVSKSLAEKAAW |
| SEQ ID NO: 19 | Camellia | KAKTVKRLVFTSSAGTVNVQBHQQPVFDENNWSDLDFINKKKMTGWMYFVSKTLAEKAAW |
| SEQ ID NO: 20 | Arabidopsis | KAKTVRRFVFTSSAGTVNVEBHQKNVYDENDWSDLEFIMSKKMTGWMYFVSKSLAEKAAW |
| SEQ ID NO: 21 | Gentiana | KNKTVKKLVFTSSAGTVDVQRQQKPVYDENDWSDLDFINSTKMTGWMYFVSKILAEKAAW |
| SEQ ID NO: 22 | Ipomoea | KAKTVKRLVFTSSAGTLNVQPQQKPVYDESCWSDLDFIYAKKMTGWMYFASKILAEKAAW |
| SEQ ID NO: 23 | Vitis | AKTVRRLVFTSSAGTVNIQEHQLPVYDESCWSDMEFCRAKKMTAWMYFVSKTLAEQAAW |
| SEQ ID NO: 24 | Forsythia | KAKTVRRIVFTSSAGTVNVEEHQKSVYDETDYSDLNFIYSKKMTGWMYFVSKILAEKVAW |
| SEQ ID NO: 25 | Lycopersicon | KANTVKRLVFTSSAGTLDVQEDQKLFYDETSWSDLDFIYAKKMTGWMYFVSKILAEKAAM |
| SEQ ID NO: 26 | Bromheadia | KAGSVKRVIFTSSAGTVNVEEHQAAVYDENSWSDLHFVTRVKMTGWMYFVSKTLAEKAAM |
| SEQ ID NO: 27 | Lotus | KAKTVQRLVFTSSAGTLNAVEHQKQMYDESCWSDVEFCRRVKMTGWMYFVSKTLAEQEAW |
| SEQ ID NO: 28 | Rosa | KAKTVRRLVFTSSAGSVNVEETOKPVYNESNWSDVEFCRRVKMTGWMYFASKTLAEKAAW |
| SEQ ID NO: 29 | Glycine | KAKTVRRLIFTSSAGTLMVIERQKPVFDDTCWSDVEFCRRVKMTGWMYFVSKTLAEKEAW |
| SEQ ID NO: 30 | Zea | EAGTVRRIVFTSSAGTVNLEERQRPVYDEESWTDVDFCRRVKMTGWMYFVSKTLAEKAA |
| SEQ ID NO: 31 | Sorghum | EAGTVRRIVFTSSAGTVNIEERQRPVYDQDNWSDVDFCQRVKMTGWMYFVSKSLAEKAAW |
| SEQ ID NO: 32 | Medicago | KAKTVRRLIYTSSAGTLNVTEDQKPLWDESCWSDVEFCRRVKMTGWMYFVSKTLAEQEAW |
| SEQ ID NO: 33 | Oryza | AGTVKRIVFTSSAGTVNIEERQRPSYDHDDWSDIDFCRRVKMTGWMYFVSKSLAEKAAM |
| SEQ ID NO: 34 | Fragaria | KAKTVRRLVFTSSAGAVAIEEHPKEVYSENNWSDVVFCRKVKMTGWMYFVSKTLAEQAAW |

FIG. 3A
C.1 site
FTSSAGTVNGQEKQLHVYDESHWSDLDFIYSK
126                                                                157
      ↓  ↓    ↓↓        ↓           ↓
      V  L    MM        L           M
FIG. 3B
Ger. T132V N134L K138M Q139M E145L D152M
FIG. 3C
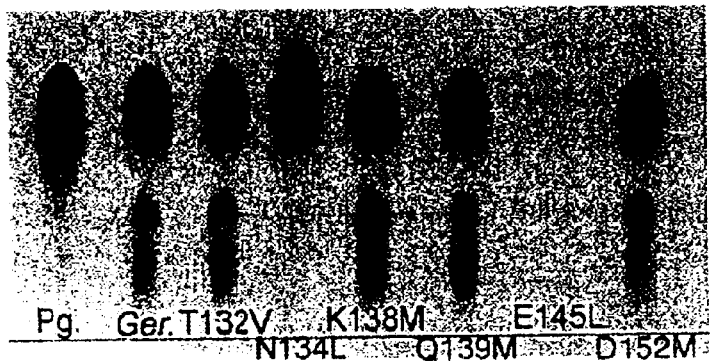
Pg. Ger. T132V K138M E145L
         N134L Q139M D152M

_US 6,660,908 B2_

GENETIC SEQUENCES ENCODING SUBSTRATE-SPECIFIC DIHYDROFLAVONOL 4-REDUCTASE AND USES THEREFOR

CROSS REFERENCE TO RELATED APPLICATIONS

This is a divisional of Ser. No. 09/638,715 filed Aug. 14, 2000, U.S. Pat. No. 6,465,630.

BACKGROUND OF THE INVENTION

1. Technical Field of the Invention

The present invention relates to modified DFR nucleic acids and encoding the modified DFR that preferentially utilize DHK as a substrate and their uses for genetically altering plants to increase the content of pelargonidin-based pigments in the plants.

2. Description of the Prior Art

Anthocyanins are classes of pigments that determine flower color and plant pigmentation in angiosperm plants. Among anthocyanins, pelargonidin-based pigments confer bric-red/orange color to plants, while cyanidin- and delphinidin-based pigments confer red and violet color each (Holton, et al. Plant Cell 7:1071–1083 (1995); Tanaka, et al. Plant Cell Physiol. 39:1119–1126 (1998)). Different ratio of these pigments confers a wide range of flower color. Many anthocyanin biosynthetic genes have been identified. One of key enzyme in the biosynthetic pathway is dihydroflavonol 4-reductase (DFR). The enzyme converts dihydroflavonols (dihydrokaempferol (DHK), dihydroquercetin (DHQ), and dihydromyricetin (DHM)) to leucocyanidins. The leucocyanidins are subsequently converted to anthocyanins by other enzymes. The conversion of DHK to DHQ and DHM are catalyzed by flavonoid 3'-hydroxylase (F3'H) and flavonoid 3',5'-hydroxylase (F3'5'H). Since DFRs in most plants can convert all three dihydroflavonols to leucocyanidins, the ratio of three classes of anthocyanin pigments are mainly determined by the activity of F3'H and F3'5'H (Holton, et al. Plant Cell 7:1071–1083 (1995)).

Since pelargonidin-based pigments confer the orange color to flowers, the F3'H and F3'5'H activities must be absent for a plant to have orange colored flowers (U.S. Pat. No. 5,410,096). In many plant species, F3'H and F3'5'H are encoded by a multiple genes, thus the mutant lines that lack F3'H and F3'5'H are not easily found. This partially accounts for the rarity of orange-colored flowers in some plant species. Inability to reduce DHK to leucocyanidin by DFR in some species can also cause the lack of orange-colored flower. For example, DFRs from Petunia and Cymbidium convert DHK to its leucocyanidin very inefficiently, thus these species do not accumulate large ratio of pelargonidin-based anthocyanins even if F3'H and F3'5'H are absent (Gerats, et al. Planta 155:364–368 (1982); Johnson, et al. Plant J. 19:81–85 (1999)). An orange-colored Petunia was engineered by introducing a maize DFR to a special mutant line of Petunia that lacks F3'H and F3'5'H (Meyer, et al. Nature 330:677–678 (1987)). Since the maize DFR can convert all three dihydroflavonols to their leucocyanidins, such a mutant line that accumulates DHK was necessary for the development of orange-colored Petunia. The necessity of the special mutant line can be circumvented by using a DFR that utilizes DHK preferentially over DHQ and DHM.

Using chimeric DFRs between Petunia and Gerbera DFRs, we identified a region that determines the substrate specificity of DFR. By altering an amino acid in the region, we developed a DHK-specific DFR that converts DHK preferentially over DHQ and DHM. When expressed in plants, the DHK-specific DFR increases the pelargonidin-based pigments regardless of F3'H activity.

SUMMARY OF THE INVENTION

Accordingly, the object of this invention is to provide substrate-specific DFRs which have point mutations at residue number 134 of SEQ ID NO: 2 when the amino acids are aligned with the ClustalW program.

It is an also object herein to provide a DHK-specific DFR and nucleic acids encoding the DHK-specific DFR.

Still further, it is an object herein to provide transgenic plants expressing the DHK-specific DFR which confers a phenotype characterized by the increased content of pelargonidin-based pigments in the plants.

In accordance with the objects, the invention includes the modified DFRs and nucleic acids encoding the modified DFRs which have altered amino acid sequences at the substrate specificity determining region. The properties of modified DFRs are characterized by their abilities to reduce one substrate preferentially among DHK, DHQ, and DHM.

The invention also includes a modified DFR that reduces DHK preferentially over DHQ and DHM.

The invention also includes plants having at least one cell transformed with a vector comprising at least a portion of the modified DFR nucleic acids. Such plants have a phenotype characterized by the increased content of pelargonidin-based pigments.

The invention also includes vectors capable of transforming a plant cell to increase the content of pelargonidin-based pigments.

The invention also includes methods for producing plants having the increased content of pelargonidin-based pigments. The methods includes steps of transforming plant cells with vectors containing the modified DFR gene; regenerating plants from the transformed cells and selecting the plant having the increased content of pelargonidin-based-pigments.

BRIEF DESCRIPTION OF THE DRAWINGS

FIG. 2 shows the amino acid sequence of Gerbera DFR aligned with other representative DFR sequences. The ClustalW program was used to align multiple amino acid sequences (Thomson, et al. Nucl. Acids Res. 22:4673–4680 (1994)). The substrate specificity determining region is boxed and the 134$^{th}$ amino acid residue of Gerbera DFR and coressponding amino acid residues of DFRs from a few representative species are bold typed.

FIG. 3A shows site-directed mutagenesis of substrate specificity determining region. The sequence corresponds to the substrate specificity determining region of Gerbera DFR. Arrows and letters indicates amino acids that were changed to.

FIG. 3B shows flowers of transgenic Petunia expressing mutated Gerbera DFR gene. Ger indicates the wild type Gerbera DFR and T132V indicates the mutated DFR that has valine instead of threonine at the 132th position of Gerbera DFR. Names of other mutated DFRs followed the same notation rule. All transgenic lines except N134L and E145L have the same bric red colored flower. The N134L bore slightly different colored flowers and E145L bore white flowers.

FIG. 3C shows a TLC analysis of pigments produced in the transgenic Petunia flowers. As expected, the E145L did not accumulated any anthocyanin. The N134L accumulated mostly pelargonidin while other mutated DFR and wild type Gebera DFR accumulated significant amount of cyanidin and delphinidin in addition to perlargonidin.

DETAILED DESCRIPTION OF THE INVENTION

Figure 1A:
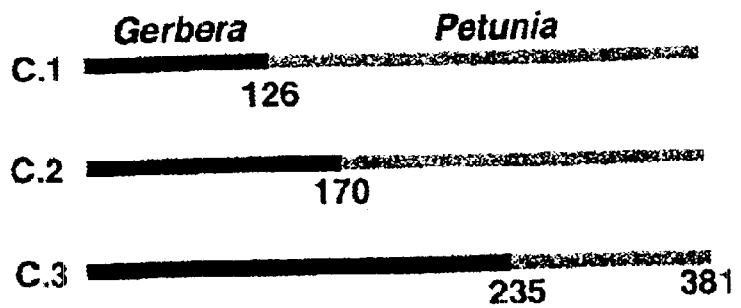
FIG. 1A is a schematic diagram showing three chimeric DFRs. Black bars indicate sequences from a Gerbera DFR and gray bars indicates sequences from a Petunia DFR. Numbers are junctional amino acid positions from the translation start site of the Gerbera DFR. C.1, C.2, C.3 are the name of three different chimeric DFRs.
Figure 1B:
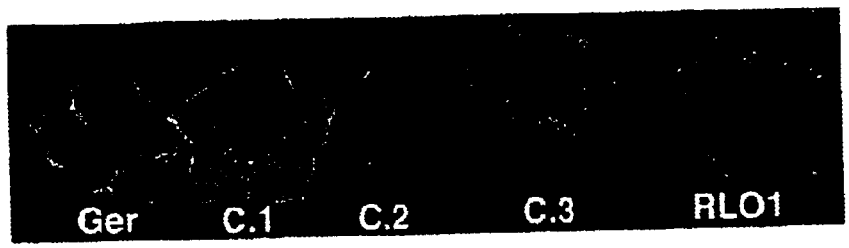
FIG. 1B shows representative flowers of transgenic Petunia expressing chimera DFRs or control DFR. Ger indicate the transgenic flower expressing Gerbera DFR and C.1, C.2, and C.3 indicate Chimera 1, Chimera 2, and Chimera 3 each. RL01 line has a functional Petunia DFR gene. The C.1 and RL01 bore similar pink colored flowers while others bore bric-red colored flower. The transgenic W80 flower expressing C.1 has pink color, while transgenic W80 flowers expressing C.2 and C.3 have orange/bric-red color. The orange/bric-red color can be also observed in the transgenic Petunia flowers expressing the native Gerbera DFR.
Figure 1C:
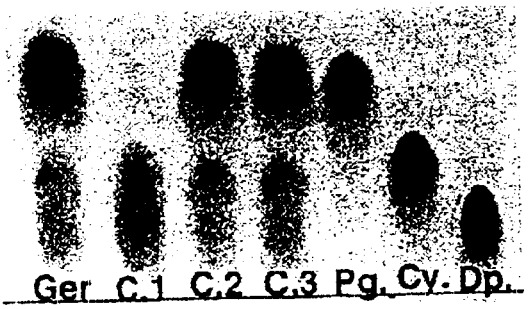
FIG. 1C shows the TLC analysis data of pigments produced in transgenic Petunia flowers next to standard pigments (pelargonidin (Pg), cyanidin (Cy), and delphinidin (Dp)). The transgenic flowers expressing C.1 has mainly cyanidin- and delphinidin-based pigments, while the flowers expressing C.2 and C.3 have mainly pelargonidin-based pigments in addition to small amount of cyanidin- and delphinidin-based pigments.

In accordance with the present invention, the substrate specificity determining region was identified by determining the abilities of three chimeric DFRs to catalyze the reduction of DHK in the transgenic Petunia lines. In order to identify the region of DFR that determines its substrate specificity, we constructed chimeric DFR genes using cDNA sequences of Petunia (SEQ ID NO: 35) and Gerbera (SEQ ID NO: 1). Though these two DFRs have high similiarity at the amino acid level, Gerbera DFR is able to catalyze dihydrokaempferol (DHK) while Petunia DFR cannot (Elomaa et al. Mol. Gen. Genet. 248:649–656 (1995)). We built three different chimeric genes using regions of high homology as common PCR primer sites (FIG. 1A). The chimeric genes were transformed into a white flowered Petunia mutant (W80) that lacks DFR activity and accumulates primarily DHK but with appreciable amounts of dihydroquercetin (DHQ) and dihydromyricetin (DHM) (Huits et al., 1994). Chimera 1 produced pink flowers while Chimeras 2 and 3 bore orange-pink flowers (FIG. 1B). The hue of Chimera 1 flowers is very similar to the inbred Petunia mutant RLO1, which has functional DFR activity and accumulates DHK. Thin layer chromatography (TLC) determined that Chimera 1 produced mainly cyanidin and delphinidin (FIG. 1b). Chimeras 2 and 3 primarily produced pelargonidin (FIG. 1C), which is the downstream product of DFR reduction of DHK. These results indicated that the region of DFR conferring the ability to reduce DHK was between Chimeras 1 and 2. The identified region (approx. 40 amino acids) is highly variable in DFRs from different plant species. By excluding the completely conserved amino acid sequences at the borders, the identified region is narrowed down to 26 amino acids. Hereinafter, this region is referred as substrate specificity determining region. An example of the substrate specificity determining region in a few represenaive DFRs is shown in FIG. 2.

The invention provides the modified DFR nucleic acids and encoded DFRs that have altered amino acid sequences at the substrate specificity determining region. Such DFRs have properties characterized by the altered substrate specificity. Hereinafter, DFRs that catalyze the reduction of one substrate preferentially over other two substrates are referred as substrate-specific DFRs. In the preferred embodiments, the invention provides the modified DFR that has altered amino acid at 134$^{th}$ amino acid residue of Gerbera DFR or the corresponding amino acid residues of DFRs from other species. Such DFRs have properties characterized by catalyzing the reduction of DHK preferentially over DHQ and DHM. Hereinafter, DFRs that catalyze the reduction of DHK preferentially over DHQ and DHM are referred as DHK-specific DFRs. The 134$^{th}$ amino acid residue of Gerbera DFR and corresponding amino acid residues of DFRs from a few representative species are shown in FIG. 2.

Figure 4A:
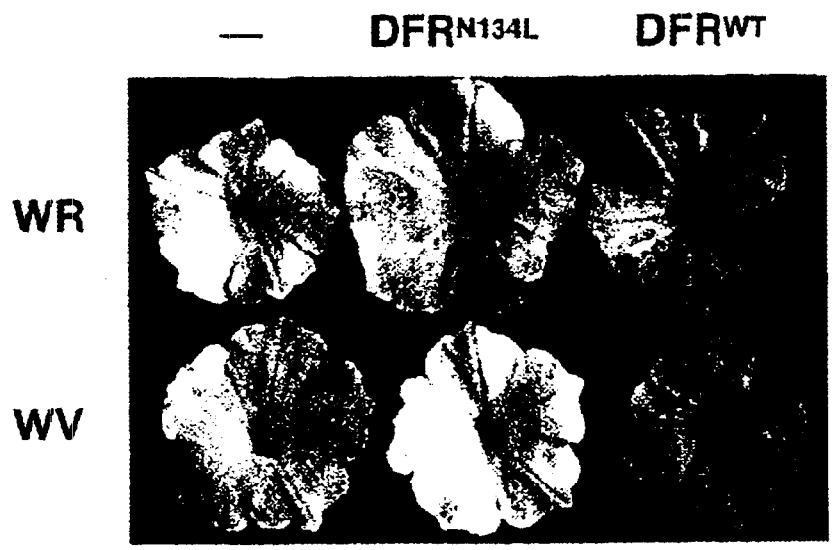
FIG. 4A shows the development of a DFR that display the altered substrate specificity. WR and WV indicate Petunia lines that are dfr$^{-/-}$, but F3'H$^{+/+}$(WR) or F3'5'H$^{+/+}$(WV). The mark – indicates no DFR gene, DFR$^{N134L}$ indicates DFR that has leucine instead of aspargine at the 134$^{th}$ position of Gerbera DFR, and DFR$^{WT}$ indicates the wild type Gerbera DFR. The flower located in the cross section indicate the WR or WV transgenic flowers expressing DFR$^{N134L}$ or DFR$^{WT}$.
Figure 4B:
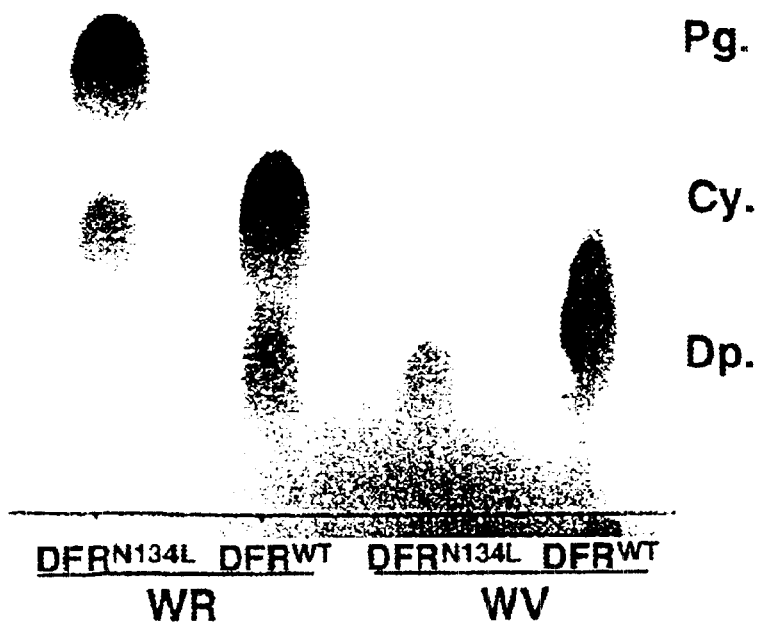
FIG. 4B shows a TLC analysis of pigments produced in the transgenic lines. Pg, Cy, and Dp indicate pelargonidin, cyanidin, and delphinidin. The WR and WV lines expressing wild type DFR accumulated cyanidin and delphinidin each. The WR line expressing DFR$^{N134L}$ accumulated pelargonidin and cyanidin, while the WV line expressing DFR$^{N134L}$ did not accumulated any pigment other than background level of delphinidin.

In accordance with the present invention, a DHK-specific DFR was developed by replacing asparagine at 134$^{th}$ amino acid residue of Gerbera DFR to leucine. The expression of the DHK-specific DFR in W80 Petunia line, which accumulates large amount of DHK in addition to appreciable amount of DHQ and DHM, caused the production of only pelargonidin. The expression of native Gerbera DFR in the same Petunia line caused the production of appreciable amounts of cyanidin and delphinidin in addition to pelargonidin (FIG. 3). Since the W80 Petunia line we transformed accumulates mainly DHK with small amount of DHQ and DHM, it was not clear if the N134L mutant DFR completely lost the capability of reducing DHQ and DHM. To investigate if the N134L mutant DFR produces only pelargonidin in the presence of fully active flavonoid-3'-hydroxylase (F3'H) or flavonoid-3',5'-hydroxylase (F3'5'H), we crossed our N134L transformant with Petunia lines that are either dfr$^{-/-}$/F3'H$^{+/+}$ (WR line) or dfr$^{-/-}$/F3'5'H$^{+/+}$ (WV line). As shown in FIG. 4A, both WR and WV lines bore white flowers as expected. When these lines were crossed with the N134L transformants, the WR line expressing the mutant DFR (WR/DFR$^{N134L}$) had orange colored flowers while the WR expressing wild type Gerbera DFR (WR/DFR$^{WT}$) had red colored flowers. Unlike the WR lines, the WV lines expressing the mutant DFR (WV/DF$^{N134L}$) bore white flowers while WV lines expressing the wild type DFR (WV/DFR$^{WT}$) had violet colored flowers. To determine the pigments produced in these crossed lines, we performed TLC analysis. FIG. 4B shows that the WR/DFR$^{N134L}$ accumulated a large amount of pelargonidin while WR/DFR$^{WT}$ mainly accumulated cyanidin. In the white flowered WV/DFR$^{N134L}$, no appreciable amounts of anthocyanidins accumulated other than a background level of delphinidin.

In contrast to WV/DFR$^{N134L}$, the WV/DFR$^{WT}$ accumulated mainly delphinidin. The data indicate that the N134L mutant DFR preferentially utilizes DHK as a substrate over DHQ and cannot reduce DHM. The substrate preference of the N134L mutant DFR is somewhat opposite to that of Petunia DFR which prefer DHM over DHQ and cannot use DHK (Forkmann and Ruhnau, 1987).The results indicates that the DHK-specific DFR can increase the pelargonidin-based pigments in plants regardless of the presence of F3'H activity.

The invention also provides plants having cells transformed with vectors comprising at least a portion of the substrate-specific DFR nucleic acids. Such plants have phenotypes characterized by the increased content of anthocyanins specified by the substrate specific DFRs. In the preferred embodiments, the invention provides plants having cells transformed with vectors comprising at least a portion of the DHK-specific DFR nucleic acids. Such plants have phenotypes characterized by the increased content of pelargonidin-based pigments. Plants that can be used to practice the invention include plants within the Division of Magnoliphyta, i.e. the angiosperms include the dicotyledons and the monocotyledons. Particularly preferred Orders of angiosperms according to "Plant Systematics", S. B. Jones, Jr. and A. E. Luchsinger include Magnoliales, Laurales, Aristolochiales, Nymphaeales, Ranunculales, Caryophyllales, Malvales, Violales, Capparales, Ericales, Primulales, Rosales, Fabales, Myrtales, Cornales, Rhamnales, Sapindales, Geraniales, Apiales, Gentianales, Solanales, Lamiales, Scrophulariales, Campanulales, Rubiales, Dipsacales, Asterales, Hydrocharitales, Arales, Cyperales, Liliales, and Orchidales. Particularly preferred plants include orchid, iris, campanula, gentiana, phlox, cyclamen, eustoma, crocus, delphinium, ageratum, chrysanthemum, Petunia, cactus, limonium, astilbe, carnation, Gerbera, brassica, impatience, geranium, dahlia, sunflower, dianthus, gloxinia, caledula, bellis, ranunculus, aster, tagetes, salvia, hibiscus, cirsium, godetia, catharanthus, alyssum, lupinus, portulaca, drotheanthus, tulip, lily, narcissus, freesia, anemone, gladiolus, caladium, archimenes, achillea, agapanthus, aethiones, allium, alstroemeria, amaryllis, anagallis, androsace, anemone, antirrhinum, aquilegia, armeria, asperula, begonia, browallia, callistephus, camellia, ceanothus, chionodoxa, cistus, clarkia, clematis, colchicun, consolida, cornus, cosmos, deutzia, digitalis, erigeron, erodium, erysimum, erythronium, felicia, gazania, gypsophila, helenium, helianthemum, heliophila, hippeastrum, hyacinthus, hydrangea, iberis, ipomoea, ixia, jacaranda, kalmia, kolkwitzia, lagerstroemia, lathyrus, lavatera, legousia, lewsia, linum, lobelia, lobularia, magnolia, malus, malva, mathiola, merendera, mimulus, myosotis, narcissus, nemesia, nicotiana, nopaixochia, nymphaea, omphalodes, orthrosanthus, osteospermum, oxalis, paeonia, pelargonium, penstemon, pentas, pericallis, persicaria, platycodon, polemonium, polygala, potentilla, primula, prunus, puschkinia, rhododendron, rhodohypoxis, rose, saintpaulia, saponaria, saxifraga, scabiosa, schizostylis, schiumbergera, schilla, sedum, senecio, silene, solanum, spiraea, stachys, streptocarpus, syringa, tagetes, tanacetum, thunbergia, thymus, torenia, tropaeolum, verbena, veronica, viburnum, vinca, viola, vitis, watsonia, and zinnia. The broad applicability of the modified DFR nucleic acids is based on the universal function of DFR in anthocyanin biosynthesis in divergent plant taxa. The parent plant used to practice the invention can be a wild type variant, a mutant which has been generated by the mutagenesis, or a transgenic line that has been generated by the recombinant techniques.

The invention also provides plant transformation vectors comprising at least a portion of substrate-specific DFR nucleic acids. In the preferred embodiments, the invention provides a plant transformation vector comprising at least a portion of DHK-specific DFR nucleic acids. Particularly preferred promoter to drive the expression of the DHK-specific DFR nucleic acids is the cauliflower mosaic virus 35S protein promoter. However, other constitutive promoters, tissue specific promoters, or inducible promoters can be also used.

The transformation of plants can be carried out in accordance with the invention by any of various transformation methods known to those skilled in the art of plant molecular biology. Particular methods for transformation include the transfer of nucleic acids into a plant cell by the microinjection, polyethylene glycol, electroporation, or microbombardment. Alternatively, plant cells can be transformed by Agrobacterium harboring vectors comprising at least a portion of modified DFR nucleic acids.

Regeneration of plants from the transformed cells can be carried out by any methods known to those skilled in the art. See, e.g., Methods in Enzymology, supra.; Methods in Enzymology, Vol 118; and Klee et al. Annual Review of Plant Physiology 38:467–486. Transformed cells or plants are selected based on their resistance to certain chemicals such as antibiotics or based on their phenotypes characterized by the increased content of pelargonidin-based pigments. The transformed plants can be self-fertilized or crossed with other plants. After the fertilization, the plants expressing at least portion of the modified DFR nucleic acids can be selected based on their resistance to certain chemicals such as antibiotics or based on their phenotypes characterized by the increased content of pelargonidin-based pigments. Alternatively, the transformed cells or a part of transformed plants can be grafted to other plants.

The following is presented as examples and is not to be construed as a limitation on the scope of the invention.

EXAMPLE

Petunia Transformation

Leaf explants of the inbred Petunia W80 line (an6$^-$, ht1$^-$, ht2$^-$, hf1$^-$, hf2$^-$, f 1$^-$, and rf) were transformed as described elsewhere except that leaf explants recently infected by *Agrobacterium tumefaciens* were rinsed with Murashige-Skoog solution containing 750 mg/L cefotaxime and then placed on media having 100 mg/L kanamycin sulfate and 500 mg/L cefotaxime (Johnson, et al. Plant J. 19:81–85 (1999)). Also, putative transformants were grown on MS media with vitamins, 30 g/L sucrose, 0.6% agar and 500 mg/L cefotaxime; after rooting the transformants were transferred to soil.

Chimeric Gene Construction

Highly conserved regions of the DFR gene were identified by a multiple sequence alignment of a number of DFRs. The 5' region (Gerbera DFR portion) of each chimeric gene was synthesized from the Gerbera DFR cDNA clone using a primer containing the codon for the starting methionine of the Gerbera DFR gene (SEQ ID NO. 5): 5'-GGC GAA AAT GGA AGA GGA TTC TCC-3' and a primer containing a conserved region of the Gerbera DFR gene (Chimera 1; SEQ ID NO: 6: 5'-AGC AGA TGA AGT GAA CAC TAG TTT CTT CAC-3'; Chimera 2; SEQ ID NO: 7: 5'-GGC TTT CTC TGC CAG AGT TTT TGA CAC GAA-3'; Chimera 3; SEQ ID NO: 8: 5'-GTG GGA CGA GCA AAT GTA TCT TCC TTT TGC-3'). The 3' region (Petunia DFR portion) of each chimeric gene was synthesized from the Petunia DFRA cDNA clone using a primer complementary to the three conserved regions (Chimera 1; SEQ ID NO: 9: 5'-TTC ACT TCA TCT GCT GGA ACT CTC GAT GTG; Chimera 2; SEQ ID NO: 10: 5'-CTG GCA GAG AAA GCC GCA ATG GAA GAA GCT-3'; Chimera 3; SEQ ID NO: 11: 5'-ATT TGC TCG TCC CAC CAT GCT ATC ATC TAC-3') and a primer containing the stop codon of the Petunia DFRA gene (SEQ ID NO: 12): 5'-GCG CTA GAC TTC AAC ATT GCT T AA-3'. 5' and 3' regions were gel purified after PCR amplification. To assemble the full length chimeric gene the 5' and 3' region fragments were added to the same tube in roughly equal amounts and subjected to PCR cycles (94° C. 30", 55° C. 30", 72° C. 1 :30). Full-length chimeric genes (~1.1 kb) were purified from agarose gels. The chimeric genes were cloned into a vector containing the 35S CaMV promoter and NOS terminator. Pfu polymerase (Stratagene, La Jolla, Calif.) was used for all PCR reactions.

Amino Acid Point Mutant Construction

Gerbera DFR genes containing one amino acid point mutation were made in a similar manner as the chimeric genes. The 5' region was synthesized using a primer having the Gerbera DFR starting methionine and a primer containing a single codon change. The 3' region was made with a complementary primer with the single codon change and a primer having the stop codon of Gerbera DFR. The full length mutant sequence was assembled like the chimeric genes above. Each point mutant was cloned into a vector having the 35S CaMV promoter and NOS terminator. The mutagenized region of each mutant DFR was sequenced to ensure the correct residue was changed. Point mutants were then transformed into the W80 Petunia line. The transformants expressing the DFR genes were crossed with WR Petunia line (dfr$^{-/-}$, F3'H$^{+/+}$) and WV Petunia line (dfr$^{-/-}$, F3'5'H$^{+/+}$) to determine the substrate specificity of the mutated DFR. Mutations in other loci were not determined in these two Petunia lines.

TLC Analysis

Anthocyanidins were separated on cellulose TLC plates as described (Johnson, et al. Plant J. 19:81–85 (1999)). Corollas were sometimes stored at 4° C. for extended periods of time in methanol-0.5% HCl solution. Before adding iso-amylalcohol, the flower extracts were quantified at 530 nm to ensure uniform loading on the TLC plate. Anthocyanin standards were purchased from Apin Chemicals Ltd. (Oxfordshire, England).

Sequence Alignment

Multiple sequence alignment of DFRs was done using ClustalW program.

What is claimed is:

1. A method for production a plant having a phenotype characterized by an increased production of leucopelapgonidin compared to wild type plants comprising the steps of:
   (i) isolating a first nucleic acid comprising SEQ ID NO: 1 encoding a dihydroflavanol-4-reductase;
   (ii) carrying out site specific mutagenesis on said first nucleic acid to produce a second nucleic acid wherein the codon for the Asn residue at position 134 has been mutated to a codon for Leu;
   (iii) introducing said second nucleic acid into a vector wherein said second nucleic acid is operable linked to a promoter
   (iv) transforming a plant cell with said vector;
   (v) regenerating the plants from one or more of said transformed plant cells;
   (vi) selecting a plant with the desired phenotype.

2. A method as recited in claim 1 wherein said first nucleic acid is from Gerbera.

3. A method as recited in claim 1 wherein said promoter is a cauliflower mosaic virus promoter.

4. A method as recited in claim 1 wherein said promoter is an inducible promoter.

5. A method as recited in claim 1 wherein said promoter is a tissue specific promoter.

* * * * *

SEQUENCE LISTING

```
<160> NUMBER OF SEQ ID NOS: 35

<210> SEQ ID NO 1
<211> LENGTH: 1101
<212> TYPE: DNA
<213> ORGANISM: Gerbera sp.
<300> PUBLICATION INFORMATION:
<301> AUTHORS: Helariutta, Y., Kotilainen, M., Elomaa, P. and Teeri,
      T. H.
<302> TITLE: Gerbera hybrida (Asteraceae) imposes regulation at several
      anatomical levels during inflorescence development on the gene
      for dihydroflavanol-4-reductase
<303> JOURNAL: Plant Mol. Biol. 28(5), 935-41
<304> VOLUME: 28
<305> ISSUE: 5
<306> PAGES: 935-941
<307> DATE: 1995-__-__
<308> DATABASE ACCESSION NUMBER: Z17221
<309> DATABASE ENTRY DATE: 1995-11-23
<313> RELEVANT RESIDUES: (31)..(1131)

<400> SEQUENCE: 1
atggaagagg attctccggc caccgtttgt gtcaccggag cggccgggtt catcggctca      60
tggctcgtca tgagacttct tgaacgtgga tacgttgttc atgcaactgt tcgtgatccc     120
ggtgacttga agaaggtgaa gcatttgcta gaactaccaa aagcacaaac aaacttgaaa     180
ttatggaaag cagatttgac acaagaagga agctttgatg aagccattca aggttgccat     240
ggtgtcttcc atctggccac tcctatggac tttgagtcca aggaccctga gaacgaaatt     300
ataaagccaa caatcgaagg ggtattaagc atcattcgat catgtgtcaa agcgaaaacc     360
gtgaagaaac tagtgttcac ctcctccgcc gggaccgtga acgacaaga gaaacaactg     420 cacgtgtacg acgaatctca ttggagcgat ttggatttta tatactctaa aaaaatgact     480
gcttggatgt atttcgtgtc aaaaactttg gctgaaaaag ctgcgtggga tgcaacgaaa     540
ggaaacaaca ttagttttat tagtatcatc ccaaccctgg tagttggtcc gtttatcacc     600
tcgacgttcc caccaagtct cgttaccgcg ctttctttga tcacgggcaa tgaagcacat     660
```

-continued

```
tattcaatta taaagcaagg tcaatatgtg cacttagatg atctttgtga gtgtcatata    720
tacctatatg agaaccctaa agcaaaagga agatacattt gttcttctca tgatgccacc    780
attcatcaat tggctaaaat catcaaagac aagtggccag agtactatat tccaaccaag    840
tttccgggga tcgatgagga gctaccgata gtttcttttt cgtcaaagaa gttaattgac    900
acgggtttcg agtttaagta taatttagag gacatgttta aaggagccat tgatacatgt    960
agagaaaagg gattgcttcc atattccaca atcaagaacc atataaatgg taaccatgtt    1020
aatggtgttc atcattatat aaaaaacaat gatgatgatc atgaaaaggg tttgctttgt    1080
tgttcaaaag aaggccaata g                                              1101
```

<210> SEQ ID NO 2
<211> LENGTH: 366
<212> TYPE: PRT
<213> ORGANISM: Gerbera sp.

<400> SEQUENCE: 2

```
Met Glu Glu Asp Ser Pro Ala Thr Val Cys Val Thr Gly Ala Ala Gly
1               5                   10                  15

Phe Ile Gly Ser Trp Leu Val Met Arg Leu Leu Glu Arg Gly Tyr Val
            20                  25                  30

Val His Ala Thr Val Arg Asp Pro Gly Asp Leu Lys Lys Val Lys His
        35                  40                  45

Leu Leu Glu Leu Pro Lys Ala Gln Thr Asn Leu Lys Leu Trp Lys Ala
    50                  55                  60

Asp Leu Thr Gln Glu Gly Ser Phe Asp Glu Ala Ile Gln Gly Cys His
65                  70                  75                  80

Gly Val Phe His Leu Ala Thr Pro Met Asp Phe Glu Ser Lys Asp Pro
                85                  90                  95

Glu Asn Glu Ile Ile Lys Pro Thr Ile Glu Gly Val Leu Ser Ile Ile
            100                 105                 110

Arg Ser Cys Val Lys Ala Lys Thr Val Lys Lys Leu Val Phe Thr Ser
        115                 120                 125

Ser Ala Gly Thr Val Asn Gly Gln Glu Lys Gln Leu His Val Tyr Asp
    130                 135                 140

Glu Ser His Trp Ser Asp Leu Asp Phe Ile Tyr Ser Lys Lys Met Thr
145                 150                 155                 160

Ala Trp Met Tyr Phe Val Ser Lys Thr Leu Ala Glu Lys Ala Ala Trp
                165                 170                 175

Asp Ala Thr Lys Gly Asn Asn Ile Ser Phe Ile Ser Ile Ile Pro Thr
            180                 185                 190

Leu Val Val Gly Pro Phe Ile Thr Ser Thr Phe Pro Pro Ser Leu Val
        195                 200                 205

Thr Ala Leu Ser Leu Ile Thr Gly Asn Glu Ala His Tyr Ser Ile Ile
    210                 215                 220

Lys Gln Gly Gln Tyr Val His Leu Asp Asp Leu Cys Glu Cys His Ile
225                 230                 235                 240

Tyr Leu Tyr Glu Asn Pro Lys Ala Lys Gly Arg Tyr Ile Cys Ser Ser
                245                 250                 255

His Asp Ala Thr Ile His Gln Leu Ala Lys Ile Lys Asp Lys Trp
            260                 265                 270

Pro Glu Tyr Tyr Ile Pro Thr Lys Phe Pro Gly Ile Asp Glu Glu Leu
        275                 280                 285

Pro Ile Val Ser Phe Ser Ser Lys Lys Leu Ile Asp Thr Gly Phe Glu
```

```
                  290             295             300
Phe Lys Tyr Asn Leu Glu Asp Met Phe Lys Gly Ala Ile Asp Thr Cys
305                 310                 315                 320

Arg Glu Lys Gly Leu Leu Pro Tyr Ser Thr Ile Lys Asn His Ile Asn
                325                 330                 335

Gly Asn His Val Asn Gly Val His His Tyr Ile Lys Asn Asn Asp Asp
                340                 345                 350

Asp His Glu Lys Gly Leu Leu Cys Cys Ser Lys Glu Gly Gln
                355                 360             365

<210> SEQ ID NO 3
<211> LENGTH: 1101
<212> TYPE: DNA
<213> ORGANISM: Gerbera sp.

<400> SEQUENCE: 3
atggaagagg attctccggc caccgtttgt gtcaccggag cggccgggtt catcggctca      60
tggctcgtca tgagacttct tgaacgtgga tacgttgttc atgcaactgt tcgtgatccc     120
ggtgacttga agaaggtgaa gcatttgcta gaactaccaa agcacaaac aaacttgaaa     180 ttatggaaag cagatttgac acaagaagga agctttgatg aagccattca aggttgccat     240
ggtgtcttcc atctggccac tcctatggac tttgagtcca aggaccctga gaacgaaatt     300
ataaagccaa caatcgaagg gtattaagc atcattcgat catgtgtcaa agcgaaaacc     360
gtgaagaaac tagtgttcac ctcctccgcc gggaccgtgc tcggacaaga gaacaactg     420 cacgtgtacg acgaatctca ttggagcgat ttggatttta tatactctaa aaaaatgact     480
gcttggatgt atttcgtgtc aaaaactttg gctgaaaaag ctgcgtggga tgcaacgaaa     540
ggaaacaaca ttagttttat tagtatcatc ccaaccctgg tagttggtcc gtttatcacc     600
tcgacgttcc caccaagtct cgttaccgcg ctttctttga tcacgggcaa tgaagcacat     660
tattcaatta taaagcaagg tcaatatgtg cacttagatg atctttgtga gtgtcatata     720
tacctatatg agaaccctaa agcaaaagga agatacattt gttcttctca tgatgccacc     780
attcatcaat tggctaaaat catcaaagac aagtggccag agtactatat tccaaccaag     840
tttccgggga tcgatgagga gctaccgata gttctttttt cgtcaaagaa gttaattgac     900
acgggtttcg agtttaagta taatttagag gacatgttta aggagccat gatacatgt      960 agagaaaagg gattgcttcc atattccaca atcaagaacc atataaatgg taaccatgtt    1020
aatggtgttc atcattatat aaaaaacaat gatgatgatc atgaaaaggg tttgctttgt    1080
tgttcaaaag aaggccaata g                                              1101

<210> SEQ ID NO 4
<211> LENGTH: 366
<212> TYPE: PRT
<213> ORGANISM: Gerbera sp.
<300> PUBLICATION INFORMATION:
<308> DATABASE ACCESSION NUMBER: Z17221
<309> DATABASE ENTRY DATE: 1995-11-23

<400> SEQUENCE: 4

Met Glu Glu Asp Ser Pro Ala Thr Val Cys Val Thr Gly Ala Ala Gly
1               5                   10                  15

Phe Ile Gly Ser Trp Leu Val Met Arg Leu Leu Glu Arg Gly Tyr Val
                20                  25                  30

Val His Ala Thr Val Arg Asp Pro Gly Asp Leu Lys Lys Val Lys His
                35                  40                  45
```

-continued

```
Leu Leu Glu Leu Pro Lys Ala Gln Thr Asn Leu Lys Leu Trp Lys Ala
    50                  55                  60

Asp Leu Thr Gln Glu Gly Ser Phe Asp Glu Ala Ile Gln Gly Cys His
65                  70                  75                  80

Gly Val Phe His Leu Ala Thr Pro Met Asp Phe Glu Ser Lys Asp Pro
                85                  90                  95

Glu Asn Glu Ile Ile Lys Pro Thr Ile Glu Gly Val Leu Ser Ile Ile
            100                 105                 110

Arg Ser Cys Val Lys Ala Lys Thr Val Lys Lys Leu Val Phe Thr Ser
        115                 120                 125

Ser Ala Gly Thr Val Leu Gly Gln Glu Lys Gln Leu His Val Tyr Asp
    130                 135                 140

Glu Ser His Trp Ser Asp Leu Asp Phe Ile Tyr Ser Lys Lys Met Thr
145                 150                 155                 160

Ala Trp Met Tyr Phe Val Ser Lys Thr Leu Ala Glu Lys Ala Ala Trp
                165                 170                 175

Asp Ala Thr Lys Gly Asn Asn Ile Ser Phe Ile Ser Ile Ile Pro Thr
            180                 185                 190

Leu Val Val Gly Pro Phe Ile Thr Ser Thr Phe Pro Pro Ser Leu Val
        195                 200                 205

Thr Ala Leu Ser Leu Ile Thr Gly Asn Glu Ala His Tyr Ser Ile Ile
210                 215                 220

Lys Gln Gly Gln Tyr Val His Leu Asp Asp Leu Cys Glu Cys His Ile
225                 230                 235                 240

Tyr Leu Tyr Glu Asn Pro Lys Ala Lys Gly Arg Tyr Ile Cys Ser Ser
                245                 250                 255

His Asp Ala Thr Ile His Gln Leu Ala Lys Ile Ile Lys Asp Lys Trp
            260                 265                 270

Pro Glu Tyr Tyr Ile Pro Thr Lys Phe Pro Gly Ile Asp Glu Glu Leu
        275                 280                 285

Pro Ile Val Ser Phe Ser Ser Lys Lys Leu Ile Asp Thr Gly Phe Glu
290                 295                 300

Phe Lys Tyr Asn Leu Glu Asp Met Phe Lys Gly Ala Ile Asp Thr Cys
305                 310                 315                 320

Arg Glu Lys Gly Leu Leu Pro Tyr Ser Thr Ile Lys Asn His Ile Asn
                325                 330                 335

Gly Asn His Val Asn Gly Val His Tyr Ile Lys Asn Asn Asp Asp
            340                 345                 350

Asp His Glu Lys Gly Leu Leu Cys Cys Ser Lys Glu Gly Gln
        355                 360                 365

<210> SEQ ID NO 5
<211> LENGTH: 24
<212> TYPE: DNA
<213> ORGANISM: Gerbera sp.

<400> SEQUENCE: 5
ggcgaaaatg gaagaggatt ctcc                                          24

<210> SEQ ID NO 6
<211> LENGTH: 30
<212> TYPE: DNA
<213> ORGANISM: Gerbera sp.

<400> SEQUENCE: 6
```

-continued

```
agcagatgaa gtgaacacta gtttcttcac                                30

<210> SEQ ID NO 7
<211> LENGTH: 31
<212> TYPE: DNA
<213> ORGANISM: Gerbera sp.

<400> SEQUENCE: 7
ggctttctct gccagagttt ttgagcacga a                              31

<210> SEQ ID NO 8
<211> LENGTH: 30
<212> TYPE: DNA
<213> ORGANISM: Gerbera sp.

<400> SEQUENCE: 8
gtgggacgag caaatgtatc ttccttttgc                                30

<210> SEQ ID NO 9
<211> LENGTH: 30
<212> TYPE: DNA
<213> ORGANISM: Petunia sp.

<400> SEQUENCE: 9
ttcacttcat ctgctggaac tctcgatgtg                                30

<210> SEQ ID NO 10
<211> LENGTH: 30
<212> TYPE: DNA
<213> ORGANISM: Petunia sp.

<400> SEQUENCE: 10
ctggcagaga aagccgcaat ggaagaagct                                30

<210> SEQ ID NO 11
<211> LENGTH: 30
<212> TYPE: DNA
<213> ORGANISM: Petunia sp.

<400> SEQUENCE: 11
atttgctcgt cccaccatgc tatcatctac                                30

<210> SEQ ID NO 12
<211> LENGTH: 24
<212> TYPE: DNA
<213> ORGANISM: Petunia sp.

<400> SEQUENCE: 12
gcgctagact tcaacattgc ttaa                                      24

<210> SEQ ID NO 13
<211> LENGTH: 60
<212> TYPE: PRT
<213> ORGANISM: Lilium sp.

<400> SEQUENCE: 13

Lys Ala Gly Thr Val Lys Arg Val Ile Phe Thr Ser Ser Ala Gly Thr
1               5                   10                  15

Val Asn Val Gln Glu Asn Gln Met Pro Glu Tyr Asp Glu Ser Ser Trp
            20                  25                  30

Ser Asp Val Asp Phe Cys Arg Arg Val Lys Met Thr Gly Trp Met Tyr
        35                  40                  45
```

```
Phe Val Ser Lys Thr Leu Ala Glu Lys Ala Ala Trp
    50                  55                  60

<210> SEQ ID NO 14
<211> LENGTH: 60
<212> TYPE: PRT
<213> ORGANISM: Hordeum sp.

<400> SEQUENCE: 14

Glu Ala Gly Thr Val Lys Arg Ile Val Phe Thr Ser Ser Ala Gly Ser
1               5                   10                  15

Val Asn Ile Glu Glu Arg Pro Arg Pro Ala Tyr Asp Gln Asp Asn Trp
                20                  25                  30

Ser Asp Ile Asp Tyr Cys Arg Arg Val Lys Met Thr Gly Trp Met Tyr
            35                  40                  45

Phe Val Ser Lys Ala Leu Ala Glu Lys Ala Ala Met
    50                  55                  60

<210> SEQ ID NO 15
<211> LENGTH: 60
<212> TYPE: PRT
<213> ORGANISM: Antirrhinum sp.

<400> SEQUENCE: 15

Gln Ala Lys Thr Val Lys Lys Phe Ile Phe Thr Thr Ser Gly Gly Thr
1               5                   10                  15

Val Asn Val Glu Glu His Gln Lys Pro Val Tyr Asp Glu Thr Asp Ser
                20                  25                  30

Ser Asp Met Asp Phe Ile Asn Ser Lys Lys Met Thr Gly Trp Met Tyr
            35                  40                  45

Phe Val Ser Lys Ile Leu Ala Glu Lys Ala Gly Met
    50                  55                  60

<210> SEQ ID NO 16
<211> LENGTH: 60
<212> TYPE: PRT
<213> ORGANISM: Petunia sp.

<400> SEQUENCE: 16

Lys Ala Asn Thr Val Lys Arg Leu Val Phe Thr Ser Ser Ala Gly Thr
1               5                   10                  15

Leu Asp Val Gln Glu Gln Gln Lys Leu Phe Tyr Asp Gln Thr Ser Trp
                20                  25                  30

Ser Asp Leu Asp Phe Ile Tyr Ala Lys Lys Met Thr Gly Trp Met Tyr
            35                  40                  45

Phe Ala Ser Lys Ile Leu Ala Glu Lys Ala Ala Met
    50                  55                  60

<210> SEQ ID NO 17
<211> LENGTH: 60
<212> TYPE: PRT
<213> ORGANISM: Callistephus sp.

<400> SEQUENCE: 17

Lys Ala Lys Thr Val Lys Lys Leu Val Tyr Thr Ser Ser Ala Gly Thr
1               5                   10                  15

Val Asn Val Gln Glu Thr Gln Leu Pro Val Tyr Asp Glu Ser His Trp
                20                  25                  30

Ser Asp Leu Asp Phe Ile Tyr Ser Lys Lys Met Thr Ala Trp Met Tyr
            35                  40                  45
```

```
Phe Val Ser Lys Thr Leu Ala Glu Lys Ala Ala Met
    50              55                  60
```

<210> SEQ ID NO 18
<211> LENGTH: 60
<212> TYPE: PRT
<213> ORGANISM: Dacus sp.

<400> SEQUENCE: 18

```
Lys Ala Lys Thr Val Lys Lys Leu Ile Tyr Thr Ser Ser Ala Gly Thr
1               5                   10                  15

Val Asn Val Arg Glu His Gln Leu Pro Val Tyr Asp Glu Ser Asn Trp
                20                  25                  30

Ser Asp Met Asp Phe Ile Tyr Ser Thr Lys Met Thr Ala Trp Met Tyr
                35                  40                  45

Phe Val Ser Lys Ser Leu Ala Glu Lys Ala Ala Trp
    50              55                  60
```

<210> SEQ ID NO 19
<211> LENGTH: 60
<212> TYPE: PRT
<213> ORGANISM: Camellia sp.

<400> SEQUENCE: 19

```
Lys Ala Lys Thr Val Lys Arg Leu Val Phe Thr Ser Ser Ala Gly Thr
1               5                   10                  15

Val Asn Val Gln Glu His Gln Gln Pro Val Phe Asp Glu Asn Asn Trp
                20                  25                  30

Ser Asp Leu Asp Phe Ile Asn Lys Lys Met Thr Gly Trp Met Tyr
                35                  40                  45

Phe Val Ser Lys Thr Leu Ala Glu Lys Ala Ala Trp
    50              55                  60
```

<210> SEQ ID NO 20
<211> LENGTH: 60
<212> TYPE: PRT
<213> ORGANISM: Arabidopsis sp.

<400> SEQUENCE: 20

```
Lys Ala Lys Thr Val Arg Arg Phe Val Phe Thr Ser Ser Ala Gly Thr
1               5                   10                  15

Val Asn Val Glu Glu His Gln Lys Asn Val Tyr Asp Glu Asn Asp Trp
                20                  25                  30

Ser Asp Leu Glu Phe Ile Met Ser Lys Lys Met Thr Gly Trp Met Tyr
                35                  40                  45

Phe Val Ser Lys Ser Leu Ala Glu Lys Ala Ala Trp
    50              55                  60
```

<210> SEQ ID NO 21
<211> LENGTH: 60
<212> TYPE: PRT
<213> ORGANISM: Gentiana sp.

<400> SEQUENCE: 21

```
Lys Ala Lys Thr Val Lys Lys Leu Val Phe Thr Ser Ser Ala Gly Thr
1               5                   10                  15

Val Asp Val Gln Glu Gln Gln Lys Pro Val Tyr Asp Glu Asn Asp Trp
                20                  25                  30

Ser Asp Leu Asp Phe Ile Asn Ser Thr Lys Met Thr Gly Trp Met Tyr
```

```
                35                  40                  45

Phe Val Ser Lys Ile Leu Ala Glu Lys Ala Ala Trp
 50                  55                  60

<210> SEQ ID NO 22
<211> LENGTH: 60
<212> TYPE: PRT
<213> ORGANISM: Ipomoea sp.

<400> SEQUENCE: 22

Lys Ala Lys Thr Val Lys Arg Leu Val Phe Thr Ser Ser Ala Gly Thr
 1               5                  10                  15

Leu Asn Val Gln Pro Gln Gln Lys Pro Val Tyr Asp Glu Ser Cys Trp
                20                  25                  30

Ser Asp Leu Asp Phe Ile Tyr Ala Lys Lys Met Thr Gly Trp Met Tyr
                35                  40                  45

Phe Ala Ser Lys Ile Leu Ala Glu Lys Glu Ala Trp
 50                  55                  60

<210> SEQ ID NO 23
<211> LENGTH: 59
<212> TYPE: PRT
<213> ORGANISM: Vitis sp.

<400> SEQUENCE: 23

Ala Lys Thr Val Arg Arg Leu Val Phe Thr Ser Ser Ala Gly Thr Val
 1               5                  10                  15

Asn Ile Gln Glu His Gln Leu Pro Val Tyr Asp Glu Ser Cys Trp Ser
                20                  25                  30

Asp Met Glu Phe Cys Arg Ala Lys Lys Met Thr Ala Trp Met Tyr Phe
                35                  40                  45

Val Ser Lys Thr Leu Ala Glu Gln Ala Ala Trp
 50                  55

<210> SEQ ID NO 24
<211> LENGTH: 60
<212> TYPE: PRT
<213> ORGANISM: Forsythia sp.

<400> SEQUENCE: 24

Lys Ala Lys Thr Val Lys Arg Ile Val Phe Thr Ser Ser Ala Gly Thr
 1               5                  10                  15

Val Asn Val Glu Glu His Gln Lys Ser Val Tyr Asp Glu Thr Asp Tyr
                20                  25                  30

Ser Asp Leu Asn Phe Ile Tyr Ser Lys Lys Met Thr Gly Trp Met Tyr
                35                  40                  45

Phe Val Ser Lys Ile Leu Ala Glu Lys Val Ala Trp
 50                  55                  60

<210> SEQ ID NO 25
<211> LENGTH: 60
<212> TYPE: PRT
<213> ORGANISM: Lycopersicon sp.

<400> SEQUENCE: 25

Lys Ala Asn Thr Val Lys Arg Leu Val Phe Thr Ser Ser Ala Gly Thr
 1               5                  10                  15

Leu Asp Val Gln Glu Asp Gln Lys Leu Phe Tyr Asp Glu Thr Ser Trp
                20                  25                  30
```

```
Ser Asp Leu Asp Phe Ile Tyr Ala Lys Lys Met Thr Gly Trp Met Tyr
        35                  40                  45

Phe Val Ser Lys Ile Leu Ala Glu Lys Ala Ala Met
 50                  55                  60

<210> SEQ ID NO 26
<211> LENGTH: 60
<212> TYPE: PRT
<213> ORGANISM: Bromheadia sp.

<400> SEQUENCE: 26

Lys Ala Gly Ser Val Lys Arg Val Ile Phe Thr Ser Ser Ala Gly Thr
 1               5                  10                  15

Val Asn Val Glu Glu His Gln Ala Ala Val Tyr Asp Glu Asn Ser Trp
                20                  25                  30

Ser Asp Leu His Phe Val Thr Arg Val Lys Met Thr Gly Trp Met Tyr
        35                  40                  45

Phe Val Ser Lys Thr Leu Ala Glu Lys Ala Ala Trp
 50                  55                  60

<210> SEQ ID NO 27
<211> LENGTH: 60
<212> TYPE: PRT
<213> ORGANISM: Lotus sp.

<400> SEQUENCE: 27

Lys Ala Lys Thr Val Gln Arg Leu Val Phe Thr Ser Ser Ala Gly Thr
 1               5                  10                  15

Leu Asn Ala Val Glu His Gln Lys Gln Met Tyr Asp Glu Ser Cys Trp
                20                  25                  30

Ser Asp Val Glu Phe Cys Arg Arg Val Lys Met Thr Gly Trp Met Tyr
        35                  40                  45

Phe Val Ser Lys Thr Leu Ala Glu Gln Glu Ala Trp
 50                  55                  60

<210> SEQ ID NO 28
<211> LENGTH: 60
<212> TYPE: PRT
<213> ORGANISM: Rosa sp.

<400> SEQUENCE: 28

Lys Ala Lys Thr Val Arg Arg Leu Val Phe Thr Ser Ser Ala Gly Ser
 1               5                  10                  15

Val Asn Val Glu Glu Thr Gln Lys Pro Val Tyr Asn Glu Ser Asn Trp
                20                  25                  30

Ser Asp Val Glu Phe Cys Arg Arg Val Lys Met Thr Gly Trp Met Tyr
        35                  40                  45

Phe Ala Ser Lys Thr Leu Ala Glu Gln Glu Ala Trp
 50                  55                  60

<210> SEQ ID NO 29
<211> LENGTH: 60
<212> TYPE: PRT
<213> ORGANISM: Glycine sp.

<400> SEQUENCE: 29

Lys Ala Lys Thr Val Arg Arg Leu Ile Phe Thr Ser Ser Ala Gly Thr
 1               5                  10                  15

Leu Asn Val Ile Glu Arg Gln Lys Pro Val Phe Asp Asp Thr Cys Trp
                20                  25                  30
```

-continued

Ser Asp Val Glu Phe Cys Arg Arg Val Lys Met Thr Gly Trp Met Tyr
         35                  40                  45

Phe Val Ser Lys Thr Leu Ala Glu Lys Glu Ala Trp
         50                  55                  60

<210> SEQ ID NO 30
<211> LENGTH: 59
<212> TYPE: PRT
<213> ORGANISM: Zea sp.

<400> SEQUENCE: 30

Glu Ala Gly Thr Val Arg Arg Ile Val Phe Thr Ser Ser Ala Gly Thr
 1               5                  10                  15

Val Asn Leu Glu Glu Arg Gln Arg Pro Val Tyr Asp Glu Glu Ser Trp
                20                  25                  30

Thr Asp Val Asp Phe Cys Arg Arg Val Lys Met Thr Gly Trp Met Tyr
         35                  40                  45

Phe Val Ser Lys Thr Leu Ala Glu Lys Ala Ala
         50                  55

<210> SEQ ID NO 31
<211> LENGTH: 59
<212> TYPE: PRT
<213> ORGANISM: Sorghum sp.

<400> SEQUENCE: 31

Glu Ala Gly Thr Val Arg Arg Ile Val Phe Thr Ser Ser Ala Gly Thr
 1               5                  10                  15

Val Asn Ile Glu Glu Arg Gln Arg Pro Val Tyr Asp Gln Asp Asn Trp
                20                  25                  30

Ser Asp Val Asp Phe Cys Gln Arg Val Lys Met Thr Gly Trp Met Tyr
         35                  40                  45

Phe Val Ser Lys Ser Leu Ala Glu Lys Ala Ala
         50                  55

<210> SEQ ID NO 32
<211> LENGTH: 60
<212> TYPE: PRT
<213> ORGANISM: Medicago sp.

<400> SEQUENCE: 32

Lys Ala Lys Thr Val Arg Arg Leu Ile Tyr Thr Ser Ser Ala Gly Thr
 1               5                  10                  15

Leu Asn Val Thr Glu Asp Gln Lys Pro Leu Trp Asp Glu Ser Cys Trp
                20                  25                  30

Ser Asp Val Glu Phe Cys Arg Arg Val Lys Met Thr Gly Trp Met Tyr
         35                  40                  45

Phe Val Ser Lys Thr Leu Ala Glu Gln Glu Ala Trp
         50                  55                  60

<210> SEQ ID NO 33
<211> LENGTH: 59
<212> TYPE: PRT
<213> ORGANISM: Oryza sp.

<400> SEQUENCE: 33

Ala Gly Thr Val Lys Arg Ile Val Phe Thr Ser Ser Ala Gly Thr Val
 1               5                  10                  15

Asn Ile Glu Glu Arg Gln Arg Pro Ser Tyr Asp His Asp Asp Trp Ser

```
                    20                  25                  30
Asp Ile Asp Phe Cys Arg Arg Val Lys Met Thr Gly Trp Met Tyr Phe
            35                  40                  45
Val Ser Lys Ser Leu Ala Glu Lys Ala Ala Met
    50                  55
```

<210> SEQ ID NO 34
<211> LENGTH: 60
<212> TYPE: PRT
<213> ORGANISM: Fragaria sp.

<400> SEQUENCE: 34

```
Lys Ala Lys Thr Val Arg Arg Leu Val Phe Thr Ser Ser Ala Gly Ala
1               5                   10                  15
Val Ala Ile Glu Glu His Pro Lys Glu Val Tyr Ser Glu Asn Asn Trp
            20                  25                  30
Ser Asp Val Val Phe Cys Arg Lys Val Lys Met Thr Gly Trp Met Tyr
            35                  40                  45
Phe Val Ser Lys Thr Leu Ala Glu Gln Ala Ala Trp
    50                  55                  60
```

<210> SEQ ID NO 35
<211> LENGTH: 3879
<212> TYPE: DNA
<213> ORGANISM: Petunia x hybrida

<400> SEQUENCE: 35

| | | | | | |
|---|---|---|---|---|---|
| attagatttt | ttaatgaact | ttaaacttga | ttccctaacc | tgttgaacgt | gttagggctt | 60 |
| ttgacctgaa | tttttaaact | attaggactc | ctcttattga | agggatgaaa | agactccta | 120 |
| attgaaatat | atctccttta | tatgacttat | cctttactta | gaggagaagt | aatagacaac | 180 |
| aataaataga | tgatcttctt | ctcacaatac | acaacacaaa | ttccacaatg | tagtcttagg | 240 |
| agaattttat | ttaggggaga | ttttttcttcc | catattatgt | acgcagttgg | ccaaactact | 300 |
| ttcaataaca | acccttttga | tatgtgtcat | tttcatattt | gattcattgt | cattaatgtt | 360 |
| tgtgtgttac | caaccgcatg | catcatgttg | ttccgatccc | aacaagtagt | atcagagcca | 420 |
| tattcaacta | atggttcgat | gagccaggtt | ataaggttga | agatatgttc | aaggcgggtt | 480 |
| cagagctgca | accaatgacg | ataataaagt | tatataaaaa | ataggatggt | aatgctacgt | 540 |
| gtggagaaaa | gtttcattca | accatatatt | caacaataat | gttgctgctg | catctttaaa | 600 |
| acaaatact | ttttaacccca | tgttttggct | acttttaacc | aatctcagtt | ttaactcatg | 660 |
| cttattttaa | tgcttgggct | ccctttttaat | ccattcttgg | gctcattttt | aacctgttgc | 720 |
| tgggcttctt | tgaaccaaaa | taatattttt | aaacatgaca | aacagcagtt | tgaagaccat | 780 |
| gtgaagaagg | aagatcaaga | ttcttttgtc | caaaattcag | gccaaggcgg | gaattgttag | 840 |
| tgttttacc | ctgaattttt | aacctattag | gactactctt | attgaaggga | tgaaaaagac | 900 |
| tcctaattag | aatatatctc | atttatatga | cttatcctta | gaggagaagt | aatagacaac | 960 |
| aataaataga | ggatcttctt | ctcacaacac | caacacaaat | tccacaatgt | agtcttagga | 1020 |
| gaattttatt | tagggagat | tttttcttcc | catattatgt | agcccagttg | gccaaactac | 1080 |
| tttcaataac | aacccttttg | atatgtgtca | ttttatatt | tgattcattg | acattatgtt | 1140 |
| tgtgtgttta | cgttccgcat | gcaccatgtt | gtttcgatcc | caacggaagg | gacacatggt | 1200 |
| aacattcaat | gccagtttct | caatttcgac | caacatccaa | aagtgatatt | gcatatatgg | 1260 |
| atgaaaatat | gtttcttcat | cacggtacga | ctcaatgatc | tttctaaaat | cggaaaattt | 1320 |

-continued

```
ctaaggactg catggttcga aactcaaaaa tgataaatat atcccttat cattctccac    1380 taaatattag gttgttcgaa cctataaatt acggctttcc acacatcacg tgttgcgtta    1440
caactaaacc aaaaccattg gaatcatgcg gagccacctt tgggcaaggg aattcaattg    1500
aaccctcttc acccgaaaat ttgtactgca ttgatatttt aaattttgaa cctcttattg    1560
aaaatcctgt ctccgtcctg cttggagcaa caacacaact ctatatgcat atgaaagagt    1620
gggtcctaag taaccagata ctacaccatc cccacagccc catttcttc tctctcagca    1680 accagtccta tttagttaat ccaatgaagt tactcaacgg gccgttgagc acgtgctcac    1740
catctaacat tcccaatcct tagacaacct acgtgcaagt actataaaga cagatataaa    1800
ccaacacata aataaagttc atcctgttgt aatttaacta ctagtaagtc cactaaaatt    1860
aacaaaatct taagtccgac tttccaactt ccatatctga taatggcaag tgaagcagtt    1920
catgcccctt cacctccggt ggcagtgccg acagtttgcg tcactggagc tgctggattt    1980
attggctctt ggcttgtcat gagactcctt gaacgcggtt acaatgttca cgctactgtt    2040
cgtgatcctg gtatgttttg tttcgagagt ttaacttcta tgcattgcta gcgtaaaaga    2100
actttgaaag tggtatgcgc gtgaagagaa gtatgtgaca ttgataaaag tgtgcccttt    2160
gtatggcatg cacttacgta aagatgcatg attttgtaga gaacaagaag aaggtgaaac    2220
atctgctgga actgccaaag gctgatacga acttaacact gtggaaagcg acttgacag    2280 tagaaggaag ctttgacgag gccattcaag gctgtcaagg agtatttcat gtagcaacac    2340
ctatggattt cgagtccaaa gaccctgagg tacgatcaaa ctagaagcaa atatacttgt    2400 ggtccttct acatttctgg tctaaattct aacataacta tgtaactacg agatatgaca    2460
gaatgaagta atcaagccaa cagtccgggg aatgctaagc atcattgaat catgtgctaa    2520
agcaaacaca gtgaagaggc tggttttcac ttcatctgct ggaactctcg atgtgcaaga    2580
gcaacaaaaa cttttctatg accagaccag ctggagcgac ttggacttca tatatgctaa    2640
gaagatgaca ggatgggttt gtttggctat tcttttcatt tcgtaataca ctctagtaac    2700
aaaaacagca ttctcattga tacttgtgaa ttaatttcat tgcagatgta ttttgcttcc    2760
aagatactgg cagagaaagc cgcaatggaa gaagctaaaa agaagaacat tgatttcatt    2820
agcatcatac caccactggt tgttggtcca ttcatcacac ctacatttcc ccctagttta    2880
atcactgccc tttcactaat tactggtatg ctgtagtctt aaatattcta cgtaattaaa    2940
ttgcacagat gatgtgcagt tcttcctctc accaaacacc cacaaattat ttcaattaac    3000 aatatttta cagtcatggg tttaatcaga ttggggtatg cagggaatga agctcattac    3060
tgcatcatta aacaaggtca atatgtgcat ttggatgatc tttgtgaggc tcacatattc    3120
ctgtatgagc accccaaggc agatggaaga ttcatttgct cgtcccacca tgctatcatc    3180
tacgatgtgg ctaagatggt ccgagagaaa tggccagagt actatgttcc tactgagtaa    3240
gcctctctct tctgtattcc caagtatagt aggctccttc attgagtgat ggcttagtaa    3300
ctcactcgtg ggtaaataac aggtttaaag ggatcgataa agacctgcca gtggtgtctt    3360
tttcatcaaa gaagctgaca gatatgggtt ttcagttcaa gtacactttg gaggatatgt    3420 ataaagggc catcgatact tgtcgacaga agcagctgct tccctttct acccgaagtg    3480 ctgaagacaa tggacataac cgagaagcca ttgccatttc tgctcaaaac tatgcaagtg    3540
gcaaagagaa tgcaccagtt gcaaatcata cagaaatgtt aagcaatgtt gaagtctaga    3600
actgcaatct tgacaagata aagaaagctt gccaagcaat atgtttgcta ctaagttctt    3660
```

```
tgtcatctgt ttgagggttt tcaaaactaa atcagtaaat ttttcgatgc atatagagaa    3720
gttcttgtct tgctaaatta cgggcagcct aaacaatagg atatcaagaa tcccgtgcta    3780
tatttttcag gaaaataaaa tctataatca tttcagggaa tctggatact aatacaagga    3840
cgtattttcc aatttataag ctttgcaaaa gcaagatct                           3879
```